US008729226B2

(12) United States Patent
Guerra Vallespi et al.

(10) Patent No.: US 8,729,226 B2
(45) Date of Patent: May 20, 2014

(54) CANCER THERAPY METHOD

(75) Inventors: Maribel Guerra Vallespi, Havana (CU); Julio Raúl Fernández Massó, Havana (CU); Alexis Musacchio Lasa, Artemisa (CU); Jeovanis Gil Valdés, Havana (CU); Osvaldo Reyes Acosta, Havana (CU); Brizaida Maylin Oliva Argüelles, Havana (CU)

(73) Assignee: Centro de Ingenieria Genetica y Biotecnologia, Havana (CU)

( * ) Notice: Subject to any disclaimer, the term of this patent is extended or adjusted under 35 U.S.C. 154(b) by 26 days.

(21) Appl. No.: 13/700,286

(22) PCT Filed: May 31, 2011

(86) PCT No.: PCT/CU2011/000003
§ 371 (c)(1),
(2), (4) Date: Jan. 14, 2013

(87) PCT Pub. No.: WO2011/150897
PCT Pub. Date: Dec. 8, 2011

(65) Prior Publication Data
US 2013/0224313 A1    Aug. 29, 2013

(30) Foreign Application Priority Data

May 31, 2010    (CU) .................................... 2010-113

(51) Int. Cl.
*A61K 38/00*        (2006.01)
(52) U.S. Cl.
USPC ........................................................ 530/326
(58) Field of Classification Search
None
See application file for complete search history.

(56) References Cited

U.S. PATENT DOCUMENTS

2009/0221508 A1    9/2009    Guerra Vallespi
2012/0135021 A1    5/2012    Torens Madrazo

FOREIGN PATENT DOCUMENTS

WO    2007/095867    8/2007
WO    2009/021468    2/2009

OTHER PUBLICATIONS

Muller et al. (Traffic, 10:514-527, 2009).*
Biasio, "Identification of Murr1 as a Regulator of the Human δ Epithelial Sodium Channel", The Journal of Biological Chemistry. vol. 279, No. 7, Issue of Feb. 13, pp. 5429-5434, 2004, USA.
Boussif, "A versatile vector for gene and oligonucleotide transfer into cells in culture and in vivo: Polyethylenimine", Proc. Natl. Acad. Sci. USA. vol. 92, pp. 7297-7301, Aug. 1995, Biochemistry.
Burstein, "COMMD Proteins, a Novel Family of Structural and Functional Homologs of MURR1", The Journal of Biological Chemistry. vol. 280, No. 23, Issue of Jun. 10, pp. 2222-2232, 2005, USA.
Chou, "Theoretical Basis, Experimental Design, and Computerized Simulation of Synergism and Antagonism in Drug Combination Studies", Pharmacological Reviews. vol. 58, No. 3, pp. 621-681, 2006, USA.
Daelemans, "A synthetic HIV-1 Rev inhibitor interfering with the CRM-mediated nuclear export", PNAS. Oct. 29, 2002, vol. 99, No. 22, pp. 14440-14445, USA.
Geng, "Phosphorylation of NF-κB p65 at Ser468 controls its COMMD1-dependent ubiquitination and target gene-specific proteasomal elimination", EMBO reports. vol. 10, No. 4, pp. 381-386, 2009.
Granadillo, "A novel fusion protein-based vaccine comprising a cell penetrating and immunostimulatory peptide linked to human papillomavirus (HPV) type 16 E7 antigen generates potent immunologic and anti-tumor responses in mice." Vaccine 29 (2011) 920-930.
Gray, "Therapeutic Targeting of Neuropilin-2 on Colorectal Carcinoma Cells Implanted in the Murine Liver", J. Natl Cancer Inst 2008;100:109-120.
Gupta, "Inhibiting NF-κB activation by small molecules as a therapeutic strategy", Biochimica et Biophysica Acta 1799 (2010) 775-787.
Huang, "Posttranslational modifications of NF-κB: another layer of regulation for NF-κB signaling pathway", Cell Signal. Sep. 2010; 22(9): 1282-1290.
Hussain, "Inflammation and cancer: An ancient link with novel potentials", Int. J. Cancer: 121,2373-2380 (2007).
Maine, "COMMD1 promotes the ubiquitination of NF-κB subunits through a cullin-containing ubiquitin ligase", The EMBO Journal (2007) 26, 436-447.
Maine, "COMMD1 expression is controlled by critical residues that determine XIAP binding", Biochem. J. 2009 417, 601-609.
Muller, "Nuclear-Cytosolic Transport of COMMD1 Regulates NF-κB and HIF-1 Activity", Traffic 2009; 10: 514-527.
Ribble, "A simple technique for quantifying apoptosis in 96-well plates", BMC Biotechnology 2005, 5:12.
Shirley, "Combination of Proteasomal Inhibitors Lactacystin and MG132 Induced Synergistic Apoptosis in Prostate Cancer Cells", Neoplasia vol. 7, No. 12, Dec. 2005, pp. 1104-1111.
Sommerhalter, "Solution structure of the COMMD1 N-terminal domain", J Mol Biol. Jan. 19, 2007; 365(3): 715-721.
Sreedhar, "Heat shock proteins in the regulation of apoptosis: new strategies in tumor therapy. A comprehensive review", Pharmacology & Therapeutics 101 (2004) 227-257.
Tao, "The copper Toxicosis Gene Product Murr1 Directly Interacts with the Wilson Disease Protein", The Journal of Biological Chemistry, vol. 278, No. 43 Issue of Oct. 24, pp. 41593-41596, 2003.
Vallespi, "Identification of a novel antitumor peptide based on the screening of an Ala-library derived from the LALF 32-51 region", Journal of Peptide Science 2010: 16: 40-47.

(Continued)

*Primary Examiner* — Brad Duffy
*Assistant Examiner* — Nelson B Moseley, II
(74) *Attorney, Agent, or Firm* — Hoffmann & Baron LLP (57) ABSTRACT

This invention describes a method for treating cancer by increasing the nuclear localization of the COMMD1 protein, which is associated with decreasing or blocking the proliferation of the cancer cell. The invention is also related to the use of agents that increase nuclear localization of the COMMD1 protein, in the manufacture of a medicament for cancer therapy. These agents can be peptides or proteins, among other compounds. The invention is also related to the optimization of a peptide, coming from the sequence HARIKPTFR-RLKWKKYKGKFW, to increase the nuclear localization of the protein COMMD, and thus, to increase the antitumor effect of this peptide.

3 Claims, 5 Drawing Sheets

(56) References Cited

OTHER PUBLICATIONS

Van De Sluis, "Identification of a new copper metabolism gene by positional cloning in a purebred dog population", Human Molecular Genetics, 2002, vol. 11, No. 2, pp. 165-173.

Van De Sluis, "Increased Activity of Hypoxia-Inducible Factor 1 Is Associated with Early Embryonic Lethality in Commd1 Null Mice", Molecular and Cellular Biology, vol. 27, No. 11, Jun. 2007, pp. 4142-4156.

Van De Sluis, "COMMD1 disrupts HIF-1α/β dimerization and inhibits human tumor cell invasion", The Journal of Clinical Investigation, vol. 120, No. 6, pp. 2119-2130, Jun. 2010.

Vancurova, "NF-κB Activation in Tumor Necrosis Factor α-stimulated Neutrophils Is Mediated by Protein Kinase Cδ: Correlation to Nuclear IκBα", The Journal of Biological Chemistry, vol. 276, No. 23, Issue of Jun. 8, pp. 19746-19752, 2001, USA.

Vlieghe, "Synthetic therapeutic peptides: science and market", Drug Discovery Today, vol. 15, Nos. 1/2, Jan. 2010, pp. 40-56.

Vogler, "Small Molecule XIAP Inhibitors Enhance TRAIL-Induced Apoptosis and Antitumor Activity in Preclinical Models of Pancreatic Carcinoma", Cancer Research 2009;69:2425-2434.

Zoubeidi, "Clusterin Facilitates COMMD1 and I-κB Degradation to Enhance NF-κB Activity in Prostate Cancer Cells", Molecular Cancer Research 8(1); 119-30, 2010.

Zhou, "Role for Kruppel-Like Factor 4 in Determining the Outcome of p53 Response to DNA Damage", Cancer Research 2009; 69:8284-8292.

Milletti, "Cell-penetrating peptides: classes, origin, and current landscape", Drug Discovery Today 2012; 15/16:850-860.

* cited by examiner

SEQUENCE LISTING

<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 1

His Ala Arg Ile Lys Pro Thr Phe Arg Arg Leu Lys Trp Lys Tyr Lys
1               5                   10                  15

Gly Lys Phe Trp
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (6)

```
<223> OTHER INFORMATION: Xaa is Pro or Asp
<220> FEATURE:
<221> NAME/KEY: Misc_feature
<222> LOCATION: (11)
<223> OTHER INFORMATION: Xaa is Leu or Asp

<400> SEQUENCE: 2

His Ala Arg Ile Lys Xaa Thr Phe Arg Arg Xaa Lys Trp Lys Tyr Lys
 1               5                  10                  15

Gly Lys Phe Trp
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)
<223> OTHER INFORMATION: ACETYLATION
<220> FEATURE:
<221> NAME/KEY: Misc_feature
<222> LOCATION: (6)
<223> OTHER INFORMATION: Xaa is Pro or Asp
<220> FEATURE:
<221> NAME/KEY: Misc_feature
<222> LOCATION: (11)
<223> OTHER INFORMATION: Xaa is Leu or Asp

<400> SEQUENCE: 3

His Ala Arg Ile Lys Xaa Thr Phe Arg Arg Xaa Lys Trp Lys Tyr Lys
 1               5                  10                  15

Gly Lys Phe Trp
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (14)
<223> OTHER INFORMATION: Xaa is Lys or Asp
<220> FEATURE:
<221> NAME/KEY: Misc_feature
<222> LOCATION: (17)
<223> OTHER INFORMATION: Xaa is Gly or Asp

<400> SEQUENCE: 4

His Ala Arg Ile Lys Pro Thr Phe Arg Arg Leu Lys Trp Xaa Tyr Lys
 1               5                  10                  15

Xaa Lys Phe Trp
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (3)
<223> OTHER INFORMATION: Xaa is Arg or Asp
<220> FEATURE:
<221> NAME/KEY: Misc_feature
<222> LOCATION: (6)
```

<223> OTHER INFORMATION: Xaa is Pro or Asp

<400> SEQUENCE: 5

His Ala Xaa Ile Lys Xaa Thr Phe Arg Arg Leu Lys Trp Lys Tyr Lys
 1               5                  10                  15

Gly Lys Phe Trp
            20

<210> SEQ ID NO 6
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 6
catgcacgct agaatcaagc caaccttcag aagattgaag tggaagtaca agggtaagtt      60
ctggtaa                                                               67

<210> SEQ ID NO 7
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 7
gatcttacca gaacttaccc ttgtacttcc acttcaatct tctgaaggtt ggcttgattc      60
tagcgtg                                                               67

<210> SEQ ID NO 8
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 8
ttctgcagtc gaccttgagg gtggcaaa                                        28

<210> SEQ ID NO 9
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 9
cgctcgagac atcttcagtt aggctggctg atcagtgt                             38

<210> SEQ ID NO 10
<211> LENGTH: 46
<212> TYPE: DNA
<213> ORGANISM: Artificial Sequence
<220> FEATURE:
<223> OTHER INFORMATION: Synthetic Sequence

<400> SEQUENCE: 10
tgcagtcgac ccgaaaaaga aagggaaact tgagggtggc aaaccc                    46

<210> SEQ ID NO 11
<211> LENGTH: 38
<212> TYPE: DNA
<213> ORGANISM: Artificial Sequence
<220> FEATURE:

| | |
|---|---|
| <223> OTHER INFORMATION: Synthetic Sequence | |
| <400> SEQUENCE: 11 | |
| cgctcgagac atcttcagtt aggctggctg atcagtgt | 38 |

CANCER THERAPY METHOD

CLAIM OF PRIORITY

This application is the U.S. National Phase of, and Applicants claim priority from, International Application Number PCT/CU2011/000003 filed May 31, 2011 and Cuban Patent Application No. 2010-0113 filed May 31, 2010, which are incorporated herein by reference.

INCORPORATION OF SEQUENCE LISTING

Incorporated herein by reference in its entirety is the Sequence Listing for the above-identified Application. The Sequence Listing is disclosed on a computer-readable ASCII text file titled "Sequence_Listing_976_80PCTUS.txt", created on Nov. 27, 2012. The sequence.txt file is 5 KB in size.

TECHNICAL FIELD

The present invention falls within the field of biomedicine, in particular with the cancer therapy, by disclosing a new therapeutic target for anticancer drug development. These drugs, due to its greater selectivity and efficacy, contribute to the improvement in the current treatments of cancer patients. A method for the treatment of cancer through the expression and accumulation of the protein COMMD1 in the nucleus of the cancer cell is described. The chemical modifications introduced in the primary structure of the HARIKPTFRRLK-WKYKGKFW peptide increases the nuclear localization of the protein COMMD1 and the antitumor activity, in vitro and in vivo, of this peptide.

BACKGROUND OF THE INVENTION

Despite the great advances in cancer therapy, there is great interest in the development of new anticancer agents with novel mode of action, because of the development of resistance to existing anticancer drugs by tumor cells. The peptides are still of great interest as new therapeutic drugs, because of the role as mediators of important biological functions and its unique intrinsic properties that make them particularly attractive therapeutic agents. The peptides show a high biological activity associated with low toxicity and high specificity. The benefits arising from these features include a high specificity of binding to the desired target, minimizing the adverse drug-drug interaction and reported lower tissue accumulation reducing the risk of complications due to intermediate metabolites (Vlieghe et al., 2010, Drug Discovery Today, 15:40-56). Currently, there are anti-cancer therapies that use peptides and/or small molecules with selectivity of binding to a specific target protein, which has an important biological function in cancer development. In a first scenario, these therapies can be targeted to inhibit specific protein function and cause the apoptosis of cancer cell, for example: Inhibitors of Heat Shock Proteins (HSP) (Subbarao et al., 2004, Pharmacology & Therapeutics, 101:227-257); Tyrosine kinase inhibitors (Gamido et al., 2007, Rev Med Chil, 10:1327-1332). In most of the situations these proteins are considered aberrant in the malignant process, when compared with normal tissue.

In a second scenario, the drug binds to a protein target that may or may not be aberrant in the malignant process compared to normal tissue, in this case the signaling pathways that are activated in the process of malignancy are affected, for example: Inhibitors of deoxyribonucleic acid (DNA) replication, inhibitors of microtubule assembly and inhibitors of the NFkB transcription factor.

While the first scenario is highly effective in certain hematopoietic malignancies, most of these therapies have limited effectiveness in the complexity of solid tumors. By contrast, the second scenario includes some of the most effective and more toxic cancer drugs in the oncologic pharmacopoeia. For this reason, progress is needed in the search for new drugs that are becoming more selective and effective, minimizing its toxicity. In this regard the identification of new therapeutic targets and understanding their role in cancer development, will help to identify new mechanisms of drug resistance and facilitate the design of new drugs that retain greater activity and can be combined with the existing ones, decreasing their toxicity and increasing the life quality of patients with cancer. COMMD1 protein, previously known as MURR1 (van de Sluis et al., 2002, Human Molecular Genetics, 11:165-173) belongs to a new family of proteins, known by its acronym COMMD (Copper Metabolism gene MURR1 Domain, COMMD abbreviated). The ten members of the family proteins are highly conserved in pluricellular organisms and ubiquitously expressed, but the biological functions of most of its members are unknown. The key characteristic of this family is the presence of the COMM domain (Copper Metabolism Murr1 Domain), conserved and unique, comprising the amino acid residues 110-190 of the C-terminal region (Burstein et al., 2005, The Journal of Biological Chemistry, 280:22222-22232). COMMD1 has been implicated in diverse biological processes such as: the control of copper metabolism (Tao et al., 2003, Journal of Biological Chemistry, 278:41593-41596), regulation of intracellular transport of sodium (Biasio et al., 2004, Journal of Biological Chemistry, 279:5429-5434), inhibition of NFkB transcriptional factor (Maine et al., 2007, The EMBO Journal, 26:436-447), inhibition of the expression of genes regulated by the Hypoxia-Inducible Factor (HIF)-1α (van de Sluis et al., 2007, Molecular and Cellular Biology, 27:4142-4156).

COMMD1 shows physical interaction with the RelA (p65) subunit from the NFkB transcriptional factor, with the catalytic-α subunit from HIF-1α factor and with Delta ENaC in epithelial sodium channels. In all cases this interaction leads to the degradation of these "client" proteins through a mechanism that involves ubiquitination and proteasome degradation pathways. It has been shown that the COMM domain is involved in protein-protein interactions, both for protein "clients" of COMMD1, as well as for interactions among family members. There is a proposal for the three-dimensional structure of the N-terminal region of COMMD1, but still there is not available a tertiary structure for the COMM domain (Sommerhalter et al., 2007, Journal of Molecular Biology, 365:715-721).

COMMD1 basal expression in the cell is controlled by ubiquitination and proteasomal degradation through a series of leucine residues, located in the COMM domain (Maine et al., 2009, Biochemical Journal, 417:601-609). Recently, it has been reported that COMMD1 has a constitutive mechanism of transport cytoplasm-nucleus through nuclear export signals (NES) also located in its COMM domain. It is reported that a disruption in the leucine sequence and/or agents that inhibit the proteasomal degradation, generates an increasing in the expression of COMMD1 in the cells. In addition, the disruption of the NES sequences in COMMD1 increases the repression of the transcriptional activity of NFkB and HIF-1α factors (Muller et al., 2009, Traffic, 10:514-527).

The cancer cells over-expressing different proteins, such as the protein XIAP (X-linked inhibitor of apoptosis) and secretory clusterin (sCLU). Both proteins promote degradation of COMMD1 and facilitate the activation of NFkB and tumor cell survival. It is reported that proteasome inhibitors, such as MG132 (Shirley et al., 2005, Neoplasia, 7:1104-1111; Zhou et al., 2009, Cancer Research, 21:333-339) showed antitumor effect by inhibiting the mechanism of ubiquitination and proteasome degradation. Compounds that bind to XIAP induce apoptosis by blocking the inhibitory effect of this protein on the activation of caspase-3 and caspase-9 (Vogler et al., Cancer Research, 2009, 69:2425-2434). It is suggested that the interference ribonucleic acid (RNAi) designed to inhibit the function of sCLU has antitumor effect, by stabilizing a cytoplasmic inhibitor of NFkB factor known as I-kB (Zoubeidi et al., 2010, Molecular Cancer Research, 8:19-30).

In the international patent application WO 07/095,867, the essence of the invention is related to peptides derived from the 32-51 region of the LALF protein (Limulus anti-lipopolysaccharide factor), in which amino acid substitutions were made to ensure dissociation of the LPS-binding capacity and increase the antitumor and immunomodulatory activities. One of these peptides is the peptide named L2. In addition, another invention (International Application PCT/CU2008/000006) reveals the cell-penetrating ability of the above mentioned peptides. However, in such inventions is not disclosed nor suggested the mechanism of action of such peptides.

At present there are a number of therapies to treat cancer (chemotherapy, radiotherapy, immunotherapy, etc), many of which are in clinical trials. However, there are still drawbacks associated with these therapies such as: the low selectivity, toxicity and development of drug resistance. Another important aspect to consider in this area is the selection of biomarkers, useful as diagnostic and/or as predictors of drug efficacy. Therefore, there remains a need to investigate and discover new molecules that are useful in the treatment and/or diagnosis of cancer, and the design of drugs more selective and effective with less toxicity.

DESCRIPTION OF THE INVENTION

The present invention solves the problem above mentioned, by describing a method for the treatment of cancer by increasing the nuclear localization of the protein COMMD1. This increase causes a reduction or blockage of the proliferation of cancer cells.

In this invention is revealed, for the first time, that the L2 peptide (with the sequence HARIKPTFRRLKWKKYKGKFW, SEQ ID No. 1) and COMMD1 interact in the cells, and that nuclear localization of COMMD1 is associated with cancer cell death. Thus, the present invention provides the use of the protein COMMD1 in the identification of compounds with antitumor activity that facilitates the nuclear localization and accumulation of COMMD1.

The data provided in this invention show that the L2 peptide interacts with COMMD1, specifically in the region between amino acids 110-190. In addition, the L2 peptide produces nuclear accumulation of COMMD1. Furthermore, for the first time is reported in this invention that expression of the COMMD1 protein bearing nuclear localization sequences (NLS) is sufficient to induce the cell death. Therefore, the present invention demonstrates the use of COMMD1, as a therapeutic target in cancer treatment.

In addition, the peptide L552 (SEQ ID No. 3) was optimized starting from the L2 peptide (SEQ ID No. 1), to promote accumulation of the protein COMMD1 in the nucleus of cancer cells, and increase the antitumor effect of this peptide.

The peptide L552 (SEQ ID No. 3) described in this invention, that was improved to facilitate the nuclear localization of COMMD1, has the following sequence:

SEQ ID No. 3
Ac-HARIKpTFRRIKWKYKGKFW

The optimization is based on chemical modifications, done by replacing natural amino acid by unnatural amino acids (D-amino acids) in specific positions (represented in lowercase and bold in the sequence included above) and by protecting the N-terminal by acetylation (indicated as Ac- in the sequence included above). These modifications made to the L2 peptide (SEQ ID No. 1), that gave rise to the L552 peptide (SEQ ID No. 3), ensures the highest accumulation of the protein COMMD1 in the nucleus of the cells and an increase in the antitumor activity of L552 peptide, regarding the original L2 peptide. Therefore, the L552 peptide is a new class of molecules that interact with COMMD1, facilitating its nuclear localization and inhibiting the proliferation of cancer cells.

Another object of this invention is the use of agents that increase the nuclear localization of the protein COMMD1 in the manufacture of drugs for cancer therapy. Among the agents or compounds that facilitate the COMMD1 nuclear accumulation are included, for example: proteins (including antibodies), muteins, peptides, polynucleotides, aptamers, nucleic acids, and small organic molecules. These compounds can be isolated from natural sources, prepared synthetically or by recombinant technology, or any combination thereof. In a particular embodiment, the agent that increases the nuclear localization of the protein COMMD1 is the L552 peptide (SEQ ID No. 3). In the context of this invention, to increase or enhance the nuclear localization of the COMMD1 protein and to accumulate COMMD1 in the nucleus of the cells have the same meaning. In another particular embodiment, the agent that increases the nuclear localization of the COMMD1 protein can be of nucleic acid type, as an expression vector in mammalian cells containing a DNA sequence that encodes a protein COMMD1 which have introduced NLS. This type of vector can be used as gene therapy.

It is also part of the invention a pharmaceutical composition for cancer treatment comprising an agent that increases the nuclear localization of the COMMD1 protein. In one embodiment of the invention, the pharmaceutical composition comprising an effective amount of the agent that increases the nuclear localization of the COMMD1 protein (determined by its inhibitory concentration 50 ($IC_{50}$) and excipients or pharmaceutically acceptable vehicles. The composition can be administered by parenteral or topical route.

The administration of a pharmaceutical composition comprising an agent that increases the nuclear localization of the COMMD1 protein constitutes a method for treating or preventing a solid tumor in a person, wherein the method comprises the administration of an effective amount of an agent that facilitate the nuclear localization of COMMD1, to decrease or block the tumor cell growth.

In one embodiment of the invention, the agent that increases the nuclear localization of the COMMD1 protein can be administered to leukemia patients, specifically myelocytic leukemia, to block the proliferation of cancer cells. This agent can be effective, even in the presence of an inflammatory stimulus such as the bacterial lipopolysaccharide (LPS).

In the present invention is shown that the L552 peptide can be used in combination with standard chemotherapy to produce a synergistic effect and to reduce the dose of cytostatics, such as cisplatin and 5-fluorouracil (5-FU). Therefore, it is also an object of this invention a pharmaceutical combination for cancer treatment comprising one or several agents that increase the nuclear localization of the COMMD1 protein, and one or several drugs specific for the chemotherapy of cancer. In an embodiment of the invention, such agent is the L552 peptide and the specific drug for standard chemotherapy is selected between cisplatin and 5-FU. In this pharmaceutical combination the agents and drugs included in it can be administered simultaneously, separately or sequentially during the treatment.

On the other hand, recent data have expanded the concept that inflammation is a critical component of tumor progression. Today the inflammatory microenvironment is cataloged as a characteristic feature of the tumor, which ranks within the six most important features of cancer, described by Hanahan and Weinbergs (Perwez et al., 2007, Int J Cancer, 121:2373-2380).

The data provided in this invention indicate that the L552 peptide is effective in blocking the growth of cancer cells in the presence of an inflammatory stimulus. Similarly, GFP-NCOMMD1 protein (bearing Nuclear Localization Sequences) that is transiently transfected in the cancer cells, provides the same effect that the L552 peptide. More specifically, the results demonstrate that the L552 peptide promotes the cancer cell death in the presence of inflammatory stimulus such as LPS and TNF (Tumor Necrosis Factorα). Similarly, the experimental data demonstrate the effectiveness of the peptide in a murine model of colon tumor, in which mice were challenged with an inflammatory stimulus by LPS injection.

For this reason the present invention also provides a method for inhibiting the development of tumors associated with inflammation and its metastasis, comprising the administration of the L552 peptide to a person who needs it. Among tumors associated with inflammation and metastases are found, for example, the following cancers: colorectal, esophagus, lung, prostate, breast, pancreas and liver.

Also, the administration of the L552 peptide can be used, in a prophylactic manner, to prevent the development of cancer associated with chronic inflammation, such as Crohn's disease, ulcerative colitis, pancreatitis, cirrhosis, etc. Therefore, it is also an object of this invention, a method for the prevention of cancer associated with chronic inflammation, characterized by administering the L552 peptide or a composition comprising said peptide to a person who needs it.

Regarding the dose and treatment regimen to follow with the compositions comprising the L552 peptide, as an agent that increases the nuclear localization of the COMMD1 protein, an skilled person can easily determine the dose and the schedule of the treatment (prophylactic or therapeutic). The effective amount may vary depending on the relative potency of individual compositions, and may be calculated based on the molecular weight of the peptide and the in vitro $IC_{50}$ or in animal studies. For example, given the molecular weight of a compound (chemical structure) and the effective experimental dose ($IC_{50}$), a dose in mg/kg can be routinely calculated. In general, the doses are 0.2 to 4 mg/kg of weight. The peptide or the composition containing it can be administered once or several times, weekly or even for several months.

The invention also relates to the use of COMMD1 as a new prognostic marker for cancer patients, by determining the presence or absence of nuclear localization of the COMMD1 protein in a sample.

Similarly, the L552 peptide provides an active agent to treat diseases where the COMM proteins play a role or take part in the progression of the disease. This is possible, for example, in diseases where the amount of any member from the COMMD family is increased or decreased and/or its activity is increased or decreased, and this causes the disease. The ability of the L552 peptide to bind the COMM domain, comprised between the amino acid residues 110-190 of the C-terminal of COMMD proteins, supports the therapeutic activity thereof.

BRIEF DESCRIPTION OF FIGURES

FIG. 1. The figure illustrates the physical interaction between the L2 peptide and COMMD1. This was carried out by the technique of two hybrids in yeast. As negative controls were used the mating of the yeast strain AH109 transformed with the empty vector (pGBKT7) and the fragments of COMMD1 transformed with the Y187 strain. For the identification of the interaction, mating of the strain AH109 transformed with vector carrying the sequence of L2 and each COMMD1 fragment transformed into strain Y187 was carried out. As a positive control, the PCL1 mating bearing the GAL4 transcription factor was used. As it can be noted, the interaction occurs with the plasmids carrying the complete sequence of the COMMD1 gene and the construction containing the amino acids 110-190 of the COMMD1 protein.

FIG. 2. (A) The figure illustrates the validation of the interaction of L2 peptide with COMMD1 by immunoprecipitation (pulldown) in SW948 cells. In this experiment 100 µg of total protein (TP), the recombinant COMMD1 protein obtained in *Escherichia coli* (COMMD1 r) and the molecular weight standard (MW) are shown. (B) The figure illustrates the COMMD1 sub-cellular localization in SW948 cells treated with L2 peptide: COMMD1 expression in the nucleus (N), COMMD1 expression in the cytoplasm (C), untreated cells (NT). Beta Actin is showed as a cytoplasmic fraction control and human ribonuclear protein (hnRPN) as a control of the nuclear fraction.

FIG. 3. (A) The figure illustrates the higher nuclear accumulation of COMMD1 by the L552 optimized peptide. The Beta-Actin and hnRNP proteins were used as control of the cytosol and nucleus fraction, respectively. (B) The figure shows the interaction between the L552 peptide and the COMMD1 protein in different tumor cell lines, on immunoprecipitation experiments (pulldown). No interaction was detected with the Cullin 7 (CUL7) protein. The presence of Beta-Actin is shown in total protein extracts of several cell lines.

FIG. 7. (A) It is shown the chemosensitivity to 5-FU in HT-29 colon carcinoma cells transfected with GFP-N-COMMD1. The $IC_{50}$ values are shown. (B) It illustrates the effect of an inflammatory environment by addition of LPS and TN F-α on the $IC_{50}$.

EXAMPLES

Example 1

Physical Interaction Between the L2 Peptide and COMMD1

To identify anti-tumor L2 peptide-protein interactions the two-hybrid yeast system was used. For cloning the sequences corresponding to the peptide the oligonucleotides were designed as follows:

L2F:
CATGCACGCTAGAATCAAGCCAACCTTCAGAAGATTGAAGTGGAAGTACA

AGGGTAAGTTCTGGTAA

L2R:
GATCTTACCAGAACTTACCCTTGTACTTCCACTTCAATCTTCTGAAGGTT

Figure 1:
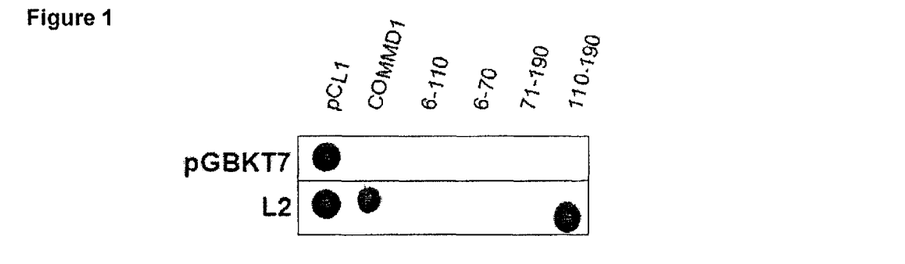

GGCTTGATTCTAGCGTG corresponding to the L2 peptide sequence: HARIKPTFRRLKWKYKGKFW
For cloning these sequences in the pGBKT7 NcoI-BamHI vector, sequences complementary to these sites were added at the ends of the oligonucleotides. The pGBKL2-1 recombinant plasmid, which carries the L2 peptide sequence was verified by restriction analysis and sequencing. The plasmid was transformed into the AH109 yeast strain by the lithium acetate method and grown in SD-Trp medium. It was verified that it could not be self-activated when grown on SD-Trp-His plates. For the screening of the interactions, a human liver cDNA library transformed into the Y187 strain was used. For the diploid formation and the selection of interactions, $5 \times 10^8$ AH109 cells containing the pGBKL2-1 plasmid were grown with $5 \times 10^8$ Y187 cells containing the human liver DNA library, for 4 hours, on solid medium YPDA at 30° C. Ten ml of sterile water were added on the surface of the YPDA plates, and the cells were suspended carefully with spatula and transferred to 15 plates of SD-Trp-Leu-His-Ade minimal media and grown at 30° C. for 7 days. The 74 resulting colonies were transferred to liquid SD-Trp-Leu in 96 deep well plates. After observing the growth in liquid medium, the purification of yeast DNA was performed. Each individual DNA was transformed into DH10B E. coli strain, their DNA purified and stored at −20° C. Each individual clone was transformed in the Y187 yeast strain and the interaction was verified by mating with the AH109 strain transformed with pGBKT7 and pGBKL2-1 plasmids. The DNA of positive clones was sequenced. The sequence analysis using the Blast program (Altschul et al., 1990. J Mol Biol, 215:403-410) revealed that one of the clones (L2-21) corresponds to the sequence of the gene coding for the amino acids 6-190 of the COMMD1 protein, and that this clone is capable to interact with the plasmid containing the L-2 peptide sequence. To specifically identify the COMMD1 protein region responsible for this interaction, deletions to the pGBKL2-1 plasmid were performed, generating the clones: pGBKL2 (6-110), pGBKL2 (6-70), pGBKL2 (71-190), pGBKL2 (110-190). As shown in FIG. 1, the interaction is preserved only in the plasmid pGBKL2 (110-190) containing the COMM domain responsible for the protein interactions described for the COMMD family. This result illustrates that the L2 peptide specifically binds the region between amino acids 110-190.

Example 2

Immunoprecipitation Experiments (Pulldown) and Determination of the Nuclear Localization of COMMD1 in Cancer Cells Treated with the Peptide L552

Figure 2:
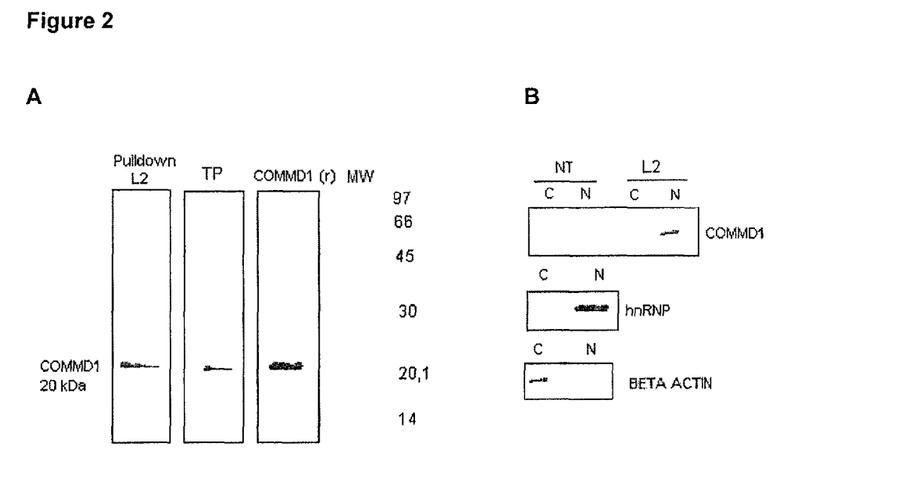

The experiments were divided into two blocks:
(A) The synthetic L2 peptide (SEQ ID No. 1), synthesized using a solid phase procedure was biotinylated and used as "bait" attached to a streptavidin sepharose resin. Total extract protein from SW948 (cell line from human colon carcinoma) was used as a "prey". These experiments are known as "pulldown". The total extract protein was obtained from $2 \times 10^7$ cells using extraction buffer (Triton X-100 0.5% 25 mM HEPES, pH 7.5, 100 mM NaCl, 1 mM EDTA, 10% glycerol, 1 mM dithiothreitol (DTT), and a protease inhibitor). The biotinylated peptide (300 μg) was incubated with 50 μL of streptavidin sepharose resin (GE Healthcare), for 1 hour, and washed with phosphate buffered saline (PBS 1×) plus 1 mM DTT were done. Then, 500 μL of total proteins were incubated with 50 μL resin containing the biotinylated peptide, at room temperature for 5 hours. Subsequently, the resin is washed extensively with PBS 1× and 1 mM DTT. Proteins remaining attached to the resin are those that interact with the peptide, and are suspended in 25 μL of electrophoresis buffer (62.5 mM Tris HCl, pH 6.9, 0.1 M DTT, 20% sodium dodecyl-sulphate (SDS), 10% glycerol and 0.01% bromophenol blue). To detect the protein of interest a polyacrylamide gel electrophoresis (7.5%) was performed, followed by immunodetection by Western blot. To detect the COMMD1 protein, a monoclonal antibody against COMMD1 protein (Sigma, clone 2A12) was used. Total protein extract (100 μg) and the recombinant COMMD1 protein obtained in E. coli were employed as positive control. The results presented in FIG. 2A show that the L2 peptide concentrates the COMMD1 protein in the pulldown experiment when it is compared to the total protein extract. This indicates the interaction between the L2 and COMMD1.

(B) SW948 cells ($3 \times 10^6$ cells) were incubated for 5 hours at 37° C. and 5% $CO_2$ with the L2 peptide (50 μM). Subsequently, cytosolic and nuclear proteins were obtained as reported (Vancurova et al., 2001, Journal of Biological Chemistry, 276: 19746-19752). The COMMD1 detection was performed by Western blot using an anti-COMMD1 antibody. The FIG. 2B shows the COMMD1 nuclear localization in SW948 cells treated with L2 peptide. Beta Actin was used as a control for the cytoplasmic fraction and the human ribonucleoprotein (hnRNP) as a control of the nuclear fraction.

Example 3

Optimization of L552 Peptide for Nuclear Accumulation of COMMD1

Considering that the peptide L2 and COMMD1 have a physical interaction, and this correlated with the nuclear localization of COMMD1, several peptides were designed starting from L2 (SEQ ID No. 1), with the aim of enhancing the nuclear accumulation of COMMD1. The peptides of this invention were synthesized using a solid phase procedure.

The crude peptide is extracted with a solution of 30% acetic acid; it is lyophilized and then purified by reverse phase chromatography RP-HPLC. The molecular mass of purified peptides was verified by mass spectrometry. The resulting preparation is non-antigenic, non-pyrogenic and pharmaceutically acceptable for administration in animals and humans. Substitutions were made on certain points, introducing D-amino acids in specific positions in the original L2 peptide, whose sequence is HARIKPTFRRLKWKYKGKFW (SEQ ID No. 1), as shown in Table 1. In one case, the N-terminal was also blocked by acetylation.

TABLE 1

Sequence of peptides used in the invention

| Peptide | Amino acid sequence | SEQ ID No. | Features |
|---|---|---|---|
| L2 | HARIKPTFRRLKWKYKGKFW | 1 | Peptide previously described in application WO 07/095 867 |
| L551 | HARIKpTFRRIKWKYKGKFW | 2 | Peptide with D-amino acids at positions P-6 and L-11 |
| L552 | Ac-HARIKpTFRRIKWKYKGKFW | 3 | Peptide with D-amino acids at positions P-6 and L-11, and acetylated in the N-terminal |
| L553 | HARIKPTFRRLKWkYKgKFW | 4 | Peptide with D-amino acids at positions K-14 and G-17 |
| L554 | HArlKpTFRRLKWKYKGKFW | 5 | Peptide with D-amino acids at positions R-3 and P-6. |

Note:
the amino acids in bold and lower case mean D-amino acid changes

Figure 3:
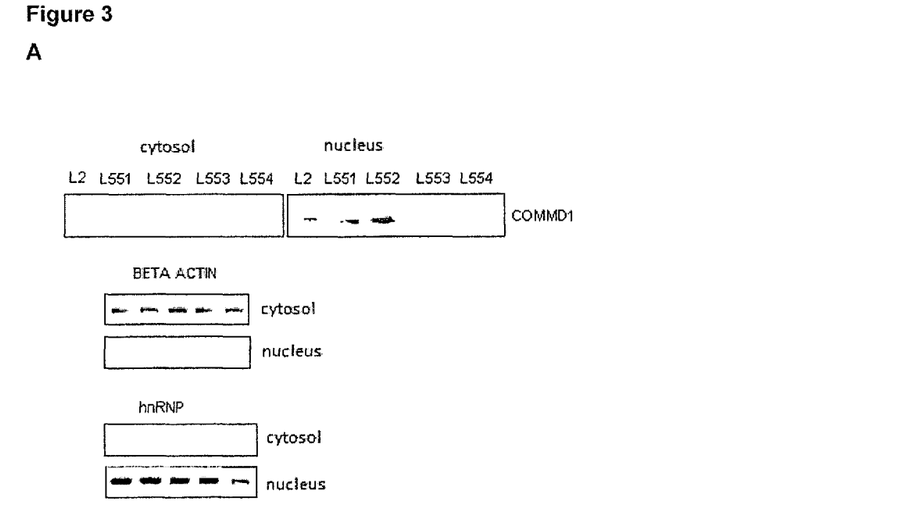

In this experiment the objective was to identify a peptide with a higher capacity to accumulate COMMD1 in the nucleus of the cells. SW948 cells ($3\times10^6$ cells) were incubated for 5 hours at 37° C. and 5% $CO_2$ with L2, L551, L552, L553 and L554 peptides (50 µM). Subsequently, isolation of cytosolic and nuclear proteins was performed as described in Example 2. COMMD1 detection was performed by Western blot using an anti-COMMD1 antibody. FIG. 3A shows the COMMD1 nuclear localization in SW948 cells treated with the above mentioned peptides. The results indicate that the L552 peptide induces the greatest accumulation of COMMD1 in the nucleus of cancer cells. Furthermore, it demonstrates the interaction between the L552 peptide and COMMD1 by immunoblotting experiments (pulldown) in different tumor lines, FIG. 3B. These results validate the interaction between the L552 and COMMD1. Also, the interaction is related to the facilitation of nuclear accumulation of COMMD1.

Example 4

Illustrate the Increase in the Antiproliferative Effect of Peptide L552 in Different Tumor Lines For this assay, the tumor cells of human origin H-82 (small cell lung cancer), H-125 (non-small cell lung cancer), MCF-7 (breast adenocarcinoma), MDA-MB231 (breast adenocarcinoma receptor-positive epidermal growth factor), LS174T (colorectal adenocarcinoma) and HT-29 (colorectal adenocarcinoma resistant to chemotherapy) were seeded in 96-well plates (Costar) at a density of $1\times10^4$ cells/mL in RPMI 1640 (Gibco) supplemented with fetal calf serum (Gibco). After 24 hours, the peptides were added to the culture medium in a dose range between 9 µM and 300 µM. The incubation was performed for 48 hours in the presence of 5% $CO_2$ and after this time, it was revealed with 3-(4,5-dimethylthiazol-2-yl) 2.5 diphenyltetrazolium bromide (MTT) (Gray M J et al., 2008, Natl Cancer Inst, 100:109-20).

Figure 4:
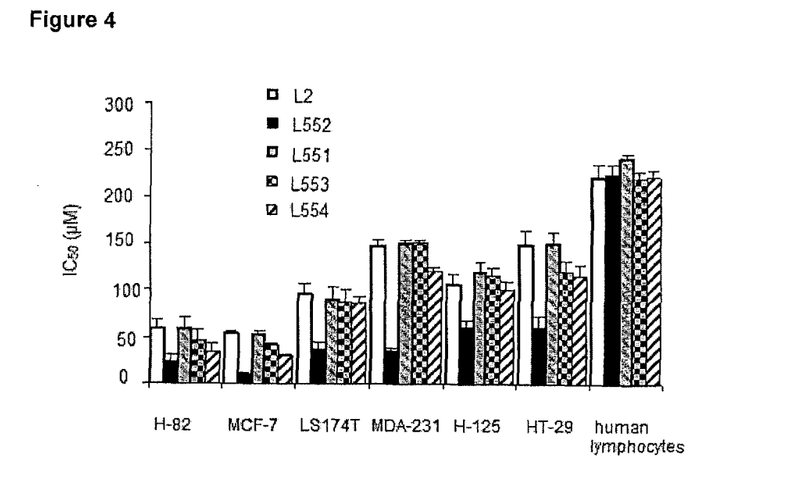
FIG. 4. Antiproliferative effect of the peptides in tumor cells of different histological origins, LØ (human lymphocytes isolated from peripheral blood).

Finally, the plate was read at an absorbance of 492 nm. Each point was performed in duplicate, and experiments were carried out independently at least twice. The $IC_{50}$ values were obtained from the respective curves of cell proliferation. The results are shown in FIG. 4. The results show that acetylation at the N-terminal and the substitution of D-amino acids at specific positions guarantee an increase in the antiproliferative effect of L552 peptide. However, no effect was observed in human lymphocytes isolated from peripheral blood. This result shows that the L552 peptide, object of this invention, enhances its selective cytotoxic effect on tumor cells without causing an increased toxicity in healthy cells. The results reported demonstrate that L552 peptide has been optimized to interact with the COMMD1 protein, to facilitate its further accumulation in the nucleus and to increase the selective antiproliferative effect on cancer cells.

Example 5

Antitumor Effect of L552 Peptide in a Murine Model of TC-1 Tumor

Figure 5:
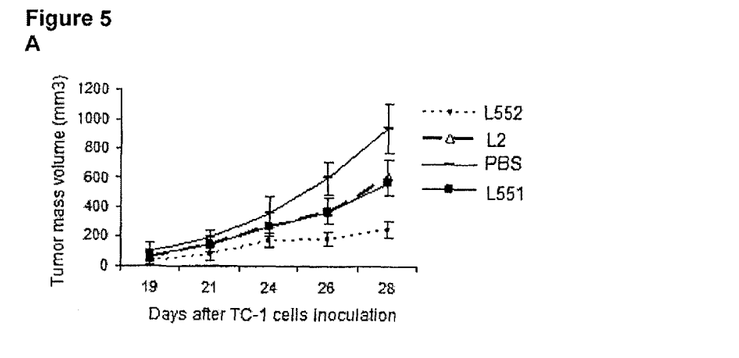
FIG. 5. Antitumor effect of the L552 peptide in the TC-1 tumor model. (A) The curves of inhibition of tumor growth are shown. (B) The cumulative percent survival of the different experimental groups are shown.

In these assays C57BL/6 female between 8 and 10 weeks of age (n=10 animals per experimental group), were used. For tumor implantation in this model, we used the TC-1 cells derived from lung epithelial cells from C57BL/6 malignant, which were suspended in saline (PBS). A quantity of $5\times10^4$ cells in a volume of 200 µL was inoculated into mice subcutaneously in the right hind leg. Five doses of peptides (L2, L552 and L551) were administered with 2-days intervals, subcutaneously in the right hind leg, once the tumors reached 100 mm3 in volume. In this study was evaluated a dose of 0.2 mg of peptide/per kg of weight (4 µg/mouse). The evaluated parameters for measuring the antitumor effect of the peptides of interest was the survival of animals and the tumor mass, as shown in FIGS. 5A and 5B. The L552 peptide was more effective in terms of ability to inhibit tumor progression and increase survival of mice compared to L2 and L551 peptides. These results evidence that the modifications introduced in the L552 increased the antitumor efficacy in vivo. Statistical analyses were performed by the log rank method to determine significant differences between groups. The results demonstrate that the L552 peptide significantly increases (*p<0.05) the survival of animals in comparison to the other peptides tested. These results demonstrate that D-amino acid substitutions in specific positions, and blocking of the N-terminal by acetylation, significantly increase the antitumor capacity of the peptide.

Example 6

Illustrates that Expression of the COMMD1 Protein Carrying Nuclear Localization Sequences is Sufficient to Induce the Cell Death To confirm the role of nuclear localization of COMMD1 on the inhibition of cell proliferation, recombinant plasmids pGFP-COMMD1, expressing COMMD1 fused to GFP, and pGFP-N-COMMD1, which also contains the PKKKRKV nuclear localization peptide sequence, was generated. For pGFP-COMMD1 cloning, the polymerase chain reaction was performed using oligonucleotides:

```
CF:
TTCTGCAGTCGACCTTGAGGGTGGCAAA

CR:
CGCTCGAGACATCTTCAGTTAGGCTGGCTGATCAGTGT
```

For amplification of the gene coding for COMMD1 with the introduction of NLS, the following oligonucleotides were used:

```
NF:
TGCAGTCGACCCGAAAAAGAAAGGGAAACTTGAGGGTGGCAAACCC

CR:
CGCTCGAGACATCTTCAGTTAGGCTGGCTGATCAGTGT.
```

The recombinant clones were analyzed by restriction and DNA sequence. Both constructs and the pEGFP control were transiently transfected in HT-29 and HEK293 cell lines using Polyethyleneimine (Sigma, USA) (Boussif, O et al., 1995, Proc Natl Acad Sci, 92: 7297-7301) in 24-well plates in duplicates. After 72 hours one of the wells was used to evaluate the expression of recombinant proteins using a fluorescence microscope Axiovert 40 (Zeiss, Germany) and APlan 10× objective.

The culture medium was removed from the remaining well and staining was performed with a mixture of acridine orange/ethidium bromide (AO/EB) at a concentration of 5 mg/mL in PBS, for identification of apoptosis (Riblah D, et al., 2005, BMC Biotechnology, 5:12-15), and they were observed under the microscope Axiovert 40 and the APlan 40× objective. With this type of staining, AO cross the membrane of live cells and stain the nucleus and cytoplasm of the cells in green and orange, respectively, while the BE only penetrates cells with membrane integrity loss and stain the DNA in red. The fluorescence of BE dominates over the AO fluorescence.

Figure 6:
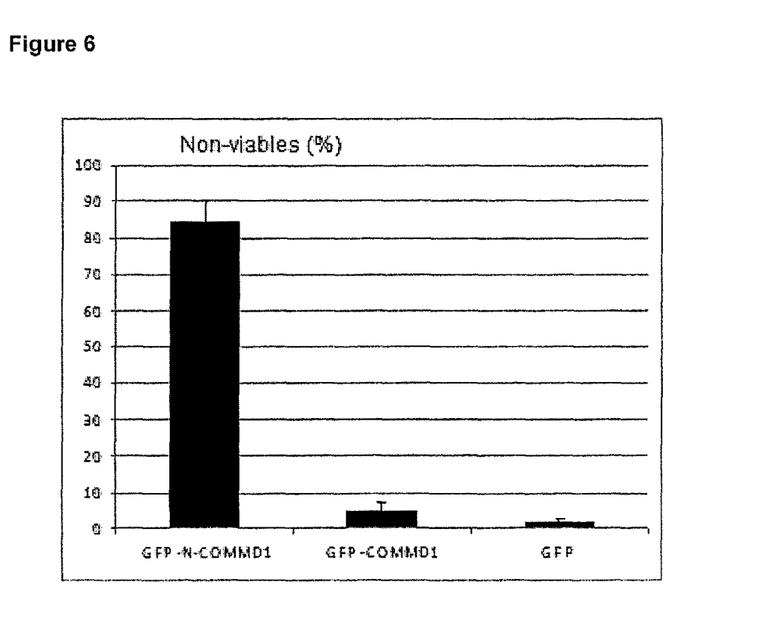
FIG. 6. The expression of the COMMD1 protein bearing nuclear localization sequences (NLS) is sufficient to induce cell death. It is shown the percentage of non viable cells transiently transfected with: green fluorescent protein (GFP) as a negative control and the genetic constructions GFP-COMMD1 and GFP-N-COMMD1.

Staining AO/EB shows viable cells stained with AO in transfections with GFP and GFP-COMMD1. Only in the case of cells transfected with GFP-N-COMMD1, cells were observed with the nucleus stained by EB, indicating that they are in a late stage of apoptosis. FIG. 6 shows the graph with the percentage of cells stained with the red nucleus, of three independent fields per experimental condition. It represents the values and standard deviations. These results demonstrate that the introduction of NLS in the protein COMMD1 is sufficient for the induction of apoptosis in the cell. These results also demonstrate the utility of COMMD1 as a new therapeutic target.

Example 7

Illustrates the Effect of the Nuclear Localization of the COMMD1 Protein in the Sensitivity to 5-FU as Well as to Inflammatory Stimuli in the Cell Line HT-29

Figure 7:
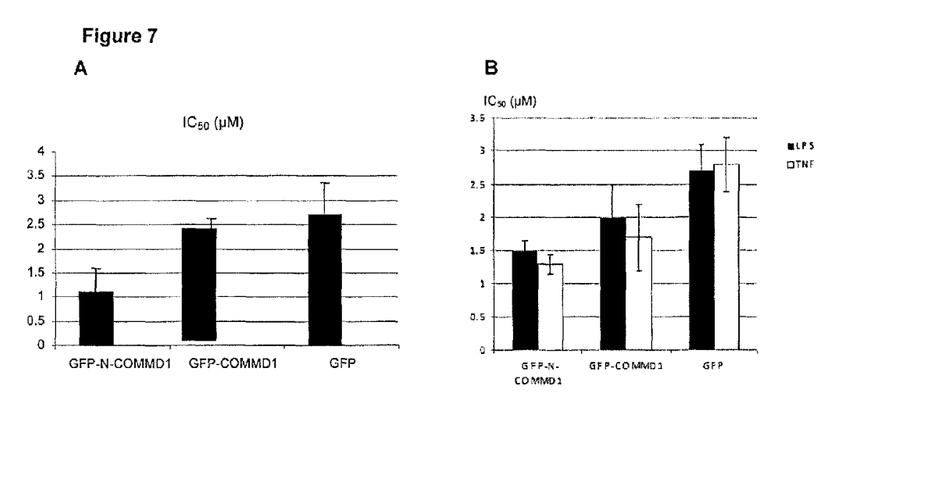

(A) The HT-29 cell line transiently transfected with constructs described above were seeded in 96-well plates (Costar) at density of $1 \times 10^4$ cells/mL in RPMI 1640 (Gibco) supplemented with fetal calf serum (Gibco) After 24 hours, the cytostatic 5-FU was added to the culture medium in a dose range between 0.025 µM and 2500 µM, in 1:10 serial dilutions. The incubation was performed for 48 hours in the presence of 5% $CO_2$ and at the end, it was revealed with MTT. Finally, the plate reading at an absorbance of 492 nm was carried out. Each point was performed in duplicate, and experiments were carried out at least twice independently. The $IC_{50}$ values were obtained from the respective curves of cell proliferation. The results presented in FIG. 7A show that the expression of COMMD1 with NLS (GFP-N-COMMD1) causes an increased sensitivity of cancer cells to 5-FU. In this example is shown a reduction of the $IC_{50}$ in the cells expressing GFP-NCOMMD1 compared to cells expressing GFP or GFP-COMMD1. These results also demonstrate the utility of COMMD1 as a new therapeutic target. It also shows that the nuclear localization of COMMD1 induces chemosensitivity to conventional cytostatics.

(B) The HT-29 cell line transiently transfected with GFP-NCOMMD1 was subjected to different inflammatory stimulus, for example LPS (40 µg/mL) and TNF-α (20 ng/mL), for 30 min. Subsequently, the $IC_{50}$ was evaluated as described in Example 6. The results are shown in FIG. 7B.

Example 8

Figure 8:
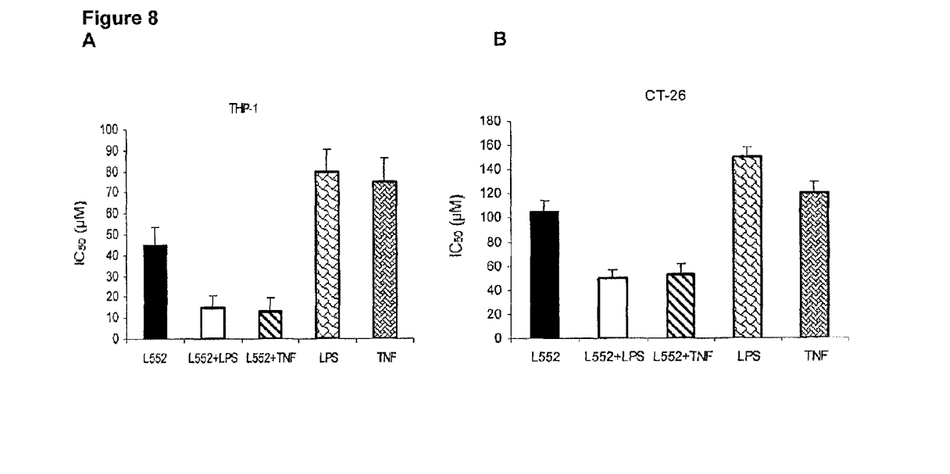
FIG. 8. It illustrates the effect of the L552 peptide on the proliferation of cancer cells in the presence of different inflammatory stimulus. (A) Human myeloid leukemia cells (THP-1) and (B) murine colon carcinoma (CT-26) treated with LPS and TNF-α. The values of $IC_{50}$ are shown.

Illustrates the Effect of L552 Peptide on Cell Proliferation of Cancer Cells Subjected to an Inflammatory Stimulus For this assay, acute myelocytic leukemia cells of human origin (THP-1) and cells of murine colon carcinoma (CT-26) were seeded in 96-well plates (Costar) at a density of $1 \times 10^4$ cells/mL in RPMI 1640 (Gibco) supplemented with 10% fetal bovine serum (FBS). Cells were maintained for 24 hrs at 37° C. and 5% $CO_2$. After this time, LPS (40 µg/mL) or TNF-α (20 ng/mL) were added for 30 min. FIG. 8 presents the $IC_{50}$ values of the THP-1 and CT-26 cell lines in the presence or absence of the above mentioned stimulus. The results show that the L552 peptide inhibits the cell proliferation in THP-1 and CT-26 cancer cell lines, in the presence of diverse inflammatory stimulus. This result shows that the L552 peptide is effective in blocking the proliferation of cancer cells subjected to different inflammatory agents.

Example 9

Illustrates the Antitumor Effect of the L552 Peptide in a Colon Cancer Model in BALB/c Mice Subjected to an Inflammatory Stimulus by LPS Injection In these assays BALB/c female mice, between 8 and 10 weeks of age (n=10 animals per experimental group) were used. For tumor implantation in this model, the CT-26 cells isolated from a colon carcinoma in BALB/c were used. A number of $7 \times 10^4$ cells, suspended in 200 µL of PBS 1×, were inoculated subcutaneously intra-axillary in the mice. After 11 days, animals received an injection of 10 μg LPS/mouse (serotype 055: B5, Sigma) in PBS, intraperitoneally administered. Once the tumors reached 100 mm³ in volume, one group received 5 doses of L552 peptide (0.2 mg/kg weight) every second day, one group received 5-FU in doses of 20 mg/kg. The parameters of interest evaluated in this experiment were the survival of animals and the increased volume of the tumor mass.

Figure 9:
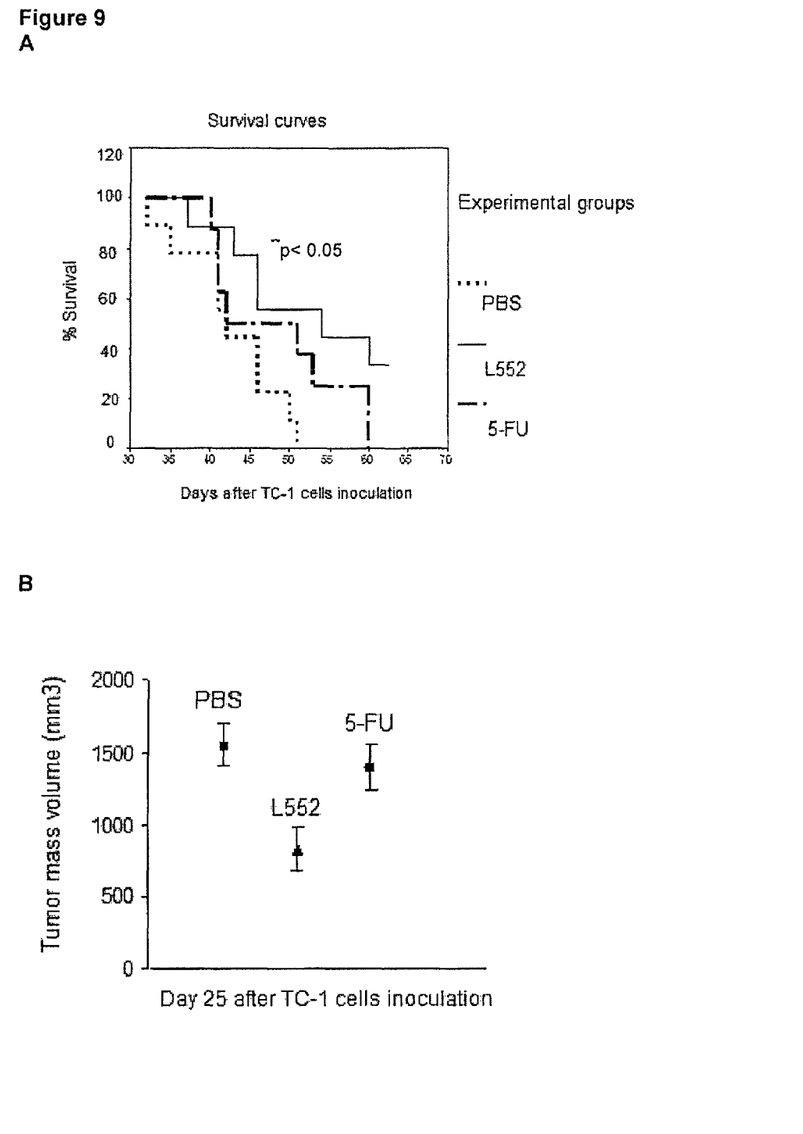
FIG. 9. Antitumor effect of the L552 peptide in a model of colon cancer in BALB/c mice subjected to an inflammatory stimulus by LPS injection. (A) Shows the cumulative percent survival of the different experimental groups. (B) Shows the average tumor volume for each experimental group.

The results presented in FIG. 9 show the efficacy of the L552 peptide in a model of colon cancer in which an inflammatory stage by injection of LPS was added. (A) The results demonstrate that L552 peptide was more effective in increasing survival (* $p < 0.05$) of animals compared with the group treated with 5-FU, when the LPS is added. The statistical analysis was performed by the log rank method, to determine significant differences between groups. (B) The L552 peptide was more effective in terms of the ability to inhibit the tumor progression. The results presented in this example shows that the L552 peptide is effective in the treatment of inflammation-associated cancer.

Example 10

Illustrates the Synergistic Effect of the Combination Between the L552 Peptide and the Standard Chemotherapy For this assay, HT-29 and H-125 tumor cells were seeded in 96-well plates (Costar) at a density of $1 \times 10^4$ cells mL in RPMI 1640 (Gibco) supplemented with fetal calf serum (Gibco). After 24 hours, the peptide was added to the culture medium in a dose range between 9 μM and 300 μM and the cytostatic drug was added in a range dose of 1:10 serial dilution over and below the reported $IC_{50}$ for each cell line. The incubation was performed for 48 hours in the presence of 5% $CO_2$ and, it was revealed with MTT. The effect of concomitant treatment cytostatic-peptide was analyzed by the CalcuSyn computer software to study drug combinations (Ting-Chao Chou, 2006, Pharmacological Reviews, 58: 621-681). The data presented in Table 2 show that the peptide-cytostatic combination can reduce the amount of cytostatic, given by the values shown in the drug reduction rate index (RI). These results indicate that the peptide can be administered in conjunction with standard chemotherapy to provide effective treatment (fraction of affected cells between 89%-94%) with a less amount of the conventional drug. The combination 5-FU+L552 peptide allows a 20 times reduction (RI) of cytostatic in the HT-29 cell line. For the combination cisplatin+L552 peptide, the cytostatic reduction is 5 times in the H-125 cell line. These results indicate that the peptide can be administered in combination with standard treatment for lung cancer and colon cancer, facilitating a reduction in the dose of cytostatic. This can reduce the adverse effects associated with chemotherapy.

TABLE 2

Synergism of the combination therapy between the L552 peptide and the cytostatics 5-FU and cisplatin, for two human tumor cell lines.

| Cell Line | Af (Afected fraction) | CI | Drug 5-FU (μM) | Drug L552 (μM) | RI (5-FU) | RI (L552) |
|---|---|---|---|---|---|---|
| HT-29 | 89% | 0.3 | 5000 | 700 | 20 | 5 |

| | Af (Afected fraction) | CI | Drug cisplatin (μM) | Drug L552 (μM) | RI (cisplatin) | RI (L552) |
|---|---|---|---|---|---|---|
| H-125 | 94% | 0.5 | 273 | 308 | 5 | 3 |

A CI < 1 means synergism,
CI = 1 indicates additivity,
CI > 1 indicates antagonism.
It also shows the reduction Index (RI) of the drug in combination.

---

The invention claimed is:

1. An isolated polypeptide consisting of the amino acid sequence of SEQ ID NO: 3, wherein the amino acids at positions 6 and 11 are D amino acids.

2. A composition comprising the polypeptide of claim 1 and a pharmaceutically acceptable excipient.

3. A composition comprising the polypeptide of claim 1 and a chemotherapeutic drug.

* * * * *

UNITED STATES PATENT AND TRADEMARK OFFICE
CERTIFICATE OF CORRECTION

PATENT NO. : 8,729,226 B2  
APPLICATION NO. : 13/700286  
DATED : May 20, 2014  
INVENTOR(S) : Maribel Guerra Vallespi et al.

Page 1 of 1

It is certified that error appears in the above-identified patent and that said Letters Patent is hereby corrected as shown below:

IN THE SPECIFICATION:

Column 1, line 58:
  Now reads: "Subbarao et al."
  Should read: -- Sreedhar et al. --

Column 1, line 60:
  Now reads: "Gamido et al."
  Should read: -- Garrido et al. --

Column 3, line 7:
  Now reads: "21:333-339"
  Should read: -- 69:8284-8292 --

Column 3, line 16:
  Now reads: "19-30"
  Should read: -- 119-130 --

Column 5, line 17:
  Now reads: "Perwez et al."
  Should read: -- Hussain --

Column 10, line 20:
  Now reads: "Natl Cancer Inst,"
  Should read: -- J. Natl Cancer Inst, --

Signed and Sealed this  
Eighteenth Day of November, 2014

Michelle K. Lee  
*Deputy Director of the United States Patent and Trademark Office*

UNITED STATES PATENT AND TRADEMARK OFFICE
CERTIFICATE OF CORRECTION

Page 1 of 1

PATENT NO.        : 8,729,226 B2
APPLICATION NO.   : 13/700286
DATED             : May 20, 2014
INVENTOR(S)       : Maribel Guerra Vallespi et al.

It is certified that error appears in the above-identified patent and that said Letters Patent is hereby corrected as shown below:

IN THE SPECIFICATION:

Column 11, line 47:
 Now reads: "Riblah"
 Should read: -- Ribble --

Column 11, line 48:
 Now reads: "5:12-15"
 Should read: -- 5:12 --

Signed and Sealed this
Seventeenth Day of March, 2015

Michelle K. Lee
*Director of the United States Patent and Trademark Office*